(12) United States Patent
Bainbridge

(10) Patent No.: US 12,263,473 B2
(45) Date of Patent: Apr. 1, 2025

(54) PROCESS FOR THE ACTIVATION OF OXIDISED CATALYSTS

(71) Applicant: JOHNSON MATTHEY DAVY TECHNOLOGIES LIMITED, London (GB)

(72) Inventor: Michael Bainbridge, Stockton-on-Tees (GB)

(73) Assignee: Johnson Matthey Davy Technologies Limited, London (GB)

( * ) Notice: Subject to any disclaimer, the term of this patent is extended or adjusted under 35 U.S.C. 154(b) by 994 days.

(21) Appl. No.: 17/272,858

(22) PCT Filed: Sep. 6, 2019

(86) PCT No.: PCT/GB2019/052485
§ 371 (c)(1),
(2) Date: Mar. 2, 2021

(87) PCT Pub. No.: WO2020/053555
PCT Pub. Date: Mar. 19, 2020

(65) Prior Publication Data
US 2021/0316295 A1 Oct. 14, 2021

(30) Foreign Application Priority Data
Sep. 10, 2018 (GB) ..................... 1814682

(51) Int. Cl.
| | | |
|---|---|---|
| *B01J 37/18* | (2006.01) | |
| *B01J 23/86* | (2006.01) | |
| *B01J 35/30* | (2024.01) | |
| *C07C 29/141* | (2006.01) | |

(52) U.S. Cl.
CPC ............. *B01J 37/18* (2013.01); *B01J 23/868* (2013.01); *B01J 35/392* (2024.01); *C07C 29/141* (2013.01)

(58) Field of Classification Search
CPC ........ B01J 37/18; B01J 35/392; B01J 23/868; C07C 29/141
USPC ....................................... 502/439
See application file for complete search history.

(56) References Cited

U.S. PATENT DOCUMENTS

| | | |
|---|---|---|
| 4,537,876 A | 8/1985 | Blum et al. |
| 4,758,546 A | 7/1988 | Baer et al. |
| 4,801,574 A | 1/1989 | Brown et al. |
| 5,481,048 A | 1/1996 | Tsukada et al. |
| 5,554,574 A | 9/1996 | Tsukada et al. |
| 5,658,843 A | 8/1997 | Tsukada et al. |
| 6,049,013 A | 4/2000 | Ueoka et al. |
| 6,303,535 B1 | 10/2001 | Scholz et al. |
| 6,410,806 B2 | 6/2002 | Oku et al. |
| 6,600,078 B1 | 7/2003 | Mahmud et al. |
| 6,680,414 B2 | 1/2004 | Knoop et al. |
| 7,524,997 B2 | 4/2009 | Kaizik et al. |
| 7,611,683 B2 | 11/2009 | Grund et al. |
| 7,803,736 B2 * | 9/2010 | Rohde .................. C08F 210/16 502/355 |
| 8,399,718 B2 | 3/2013 | Wang et al. |
| 8,603,938 B2 | 12/2013 | Sakamoto et al. |
| 8,648,005 B2 | 2/2014 | Sakamoto et al. |
| 9,006,489 B2 | 4/2015 | Gao et al. |
| 2004/0260140 A1 | 12/2004 | Loezos et al. |
| 2011/0060169 A1 | 3/2011 | Kaizik et al. |
| 2011/0160493 A1 | 6/2011 | Sakamoto et al. |
| 2011/0257452 A1 | 10/2011 | Khabashesku et al. |
| 2016/0176792 A1 | 6/2016 | Klasovsky et al. |
| 2018/0126361 A1 | 5/2018 | Klasovsky et al. |

FOREIGN PATENT DOCUMENTS

| | | |
|---|---|---|
| CN | 104151138 A | 11/2014 |
| CN | 108059588 A | 5/2018 |
| EP | 0657214 A1 | 6/1995 |
| EP | 2324922 A1 | 5/2011 |
| EP | 2 180 947 B1 | 4/2014 |
| JP | 2010-64019 A | 3/2010 |
| JP | 4661676 B2 | 3/2011 |
| WO | 2011/048361 A1 | 4/2011 |
| WO | 2016/050520 A1 | 4/2016 |

* cited by examiner

*Primary Examiner* — Edward M Johnson
(74) *Attorney, Agent, or Firm* — BakerHostetler

(57) ABSTRACT

The present invention relates to a process for the liquid phase activation of catalysts. Such activated catalysts have particular utility in hydrogenation of aldehydes to alcohols. As such, the present invention relates to a process for the hydrogenation of aldehydes to alcohols in the presence of a catalyst which has been activated in accordance with the first aspect of the present invention.

31 Claims, 2 Drawing Sheets

PROCESS FOR THE ACTIVATION OF OXIDISED CATALYSTS

The present invention relates to a process for the activation of catalysts. More particularly, the present invention relates to a process for the activation of catalysts that are for use in the hydrogenation of aldehydes to alcohols. In a further aspect, the present invention relates to a process for the hydrogenation of aldehydes to alcohols in the presence of a catalyst which has been activated in accordance with the first aspect of the present invention.

The hydrogenation of aldehydes to alcohols is practiced on an industrial scale, and it is an important part of the industrial formation of alcohols. The typical starting materials of such processes include n-butyraldehyde, iso-butyraldehyde, ethyl propyl acrolein or iso-nonyl aldehyde and the typical products include n-butanol, iso-butanol, 2-ethyl hexanol, 2-propyl heptanol and iso-nonyl alcohol.

The reaction to produce alcohols by the hydrogenation of aldehydes is highly exothermic. The heat of reaction is generally removed by circulating the aldehyde in an excess of carrier gas. One example of a process of this kind is described in Hydrocarbon Processing, March 1993, pages 67-74, the contents of which is incorporated herein by reference, or in an excess of liquid. The heat of reaction is generally removed from the circulating gas or liquid by heat exchange. There has been a focus on improving the liquid phase process because it is more commercially effective to circulate and remove heat from a liquid stream when compared with a gaseous stream, which requires specific equipment, such as compressors.

Catalysts are used in the hydrogenation of aldehydes to alcohols and are generally heterogeneous catalysts. The heterogeneous catalysts are solid and may be selected from copper, nickel and cobalt containing catalysts. Suitable copper catalysts may include promoters such as (but not limited to) nickel, chromium or zinc. The catalysts may additionally comprise manganese or barium. They may also be present on a support such as alumina, silica, chromia, zirconia or carbon.

In practice, the catalysts are supplied in either partially or totally oxidised form, so that they can be transported and installed in a rector safely. The partial oxidation will generally be surface oxidation. Once the catalyst has been installed in a reactor, it is necessary to reduce the catalyst before it can be used to catalyse the desired reaction. This process of reducing the catalyst is generally known as an activation process, or more generally as "activation". Activation is an exothermic process that is carried out by treating the catalyst with a reducing agent such as hydrogen. It is desirable that the catalyst is activated as quickly as possible to minimise the time that the reactor is out of operation.

Gas phase and liquid phase activation processes are known. There are various drawbacks associated with these activation processes.

One problem is associated with the considerable quantity of heat which is generated during the activation process. The release of heat can cause overheating either generally or locally. This overheating can result in impairment of the performance of the catalyst since sintering or crystalline growth can result. This impairment will reduce the activity of the catalyst and its ultimate lifetime.

A further problem of liquid phase processes is associated with the considerable quantity of water which is liberated during the activation process.

The presence of water and/or impairment of the catalyst through overheating can result in a less efficient process due to the incomplete conversion of the aldehyde starting material which will be observed by the presence of aldehyde in the alcohol product. This is known as aldehyde slip.

In order to avoid the drawbacks associated with liquid phase activation it is possible to use a gas phase activation process. The gas phase activation process, which by its nature is has a lower concentration of water in the gas, generally leads to a catalyst that has improved activity over that achieved with liquid phase activation processes.

Whilst a gas phase activation process generally provides a highly active catalyst, there are drawbacks associated with such processes. One problem relates to the requirement to provide large gas flow. This gas flow may be provided from an external source or it may use gas circulating within a reactor system. Where circulating gas is used, it is necessary to include equipment, including a compressor and a heat exchanger associated with the circulating gas, within the system that would not be required for liquid phase activation processes. Thus, gas phase activation processes have higher capital and operating costs than is required for liquid phase activation processes.

A further problem associated with gas phase activation processes is that additional downtime of the aldehyde hydrogenation reactor is required for cooling and wetting the catalyst, as well as establishing liquid circulation, before starting the hydrogenation of fresh reaction feed at normal operating temperatures.

In view of the problems associated with gas phase processes, liquid phase activation processes have found more favour in industrial processes.

Therefore, there remains a need for a liquid phase activation process which provides a catalyst activity which is comparable to the catalyst activity achieved with gas phase processes such that the disadvantages associated with gas phase activation processes are avoided. It has surprisingly now been found by the inventors of the present invention that if the peak water concentration present during liquid phase activation is restricted to less than 1.5 wt % (weight percent of the liquid phase) then a catalyst activity can be achieved which is higher than that achieved with conventional liquid phase activation and preferably that is equivalent to that achieved with gas phase activation.

Thus, according to a first aspect of the invention there is provided a process for the activation of a catalyst comprising:
 (a) providing a reactor comprising a solid catalyst which is to be activated by reduction;
 (b) supplying a liquid feed stream and a reducing agent to the reactor;
 (c) operating the reactor such that the reducing agent causes activation of the catalyst;
 (d) recovering a liquid stream and a gas stream from the reactor;
 and wherein, the peak water concentration in the liquid stream recovered in step (d) is substantially maintained at less than 1.5 wt % by one or more of:
 controlling the water concentration of the liquid feed stream supplied in step (b);
 controlling the rate of recovery of the liquid stream recovered in step (d); and,
 removal of water produced within the reactor.

It will be understood that the peak water concentration in the liquid stream recovered in step (d) is a measure of the peak water concentration within the reactor. Thus, the process will include measuring the peak water concentration of the stream recovered in step (d) and when it approaches a concentration of 1.5 wt % adjusting the water content of the feed and/or the flowrate of the liquid stream recovered in step (d) until the peak water concentration is maintained at less than 1.5 wt %.

By restricting the peak water concentration to less than 1.5 wt % a liquid phase activation process is provided which results in a catalyst having an increased activity compared to that achievable in liquid phase activation processes used heretofore. Preferably, the catalyst activity can be increased to at least be in the region of the level achievable for gas phase activation processes.

For example, the activity of a commercial copper/chrome catalyst for the hydrogenation of mixed butyraldehyde to butanol when activated by a gas phase activation acts such that the aldehyde slip on the start of normal operation is about 300 ppm w/w under standard test conditions. In contrast, with conventional liquid phase activations, which would result in substantial amounts of water present in the liquid phase (typically in a range of around 2.5-8 wt % depending on the reaction system configuration and volume), the aldehyde slip at the start of normal operation would be around 2300 ppm w/w. However, where the activation process of the present invention is used, the aldehyde slip is only around 360 ppm w/w and is therefore comparable to that achieved with the gas phase activation.

In the process of the present invention, the stream recovered in step (d) has a peak water concentration of less than 1.5 wt %, less than 1.4 wt %, less than 1.3 wt %, less than 1.2 wt %, less than 1.1 wt %, or less than 1.0 wt %. Preferably the liquid stream recovered in step (d) has a peak water concentration of less than 1.2 wt %, and most preferably less than 1.0 wt %.

Optionally, at least a portion of the liquid stream recovered in step (d) may be recycled and supplied to the reactor in step (b). Generally, such a recycle will not be required if the exotherm within the reactor is small, such as below 10° C., however, recycle of the liquid stream recovered in step (d) is a preferred embodiment of the present invention.

Additionally, or alternatively, the liquid stream recovered from the reactor in step (d) can be subject to a treatment and then reused (recycled) alongside the liquid feed stream to be fed to the reactor in step (b). Generally, the liquid stream removed in step (d) can be removed, treated, and then reintroduced to the liquid feed stream in step (b). Said treatment may comprise a drying process, which may be carried out by, for example, distillation, membrane separation or by the use of molecular sieves. Such a drying process will remove water from a recycled liquid stream and thus help to control the water content of the liquid stream. It is envisaged that the treatment (preferably a drying process), will be carried out extraneously to the reactor of the present invention, for example in a treatment system in a parallel loop to the reactor in which the activation process is being performed. Alternatively, although less preferred, the removed liquid stream may be removed, treated, and then stored, for example for use in a subsequent activation process, in a subsequent reaction to produce a product or otherwise recycled in some other way.

Generally, the reactor provided in step (a) will be that in which the reaction to be catalysed is to be carried out once the catalyst has been activated. That is to say that the catalyst generally will be activated in situ. The reactor may be of any configuration in which a heterogeneous catalyst can be used. The reactor may be an up-flow or a down-flow reactor. It is possible, although less preferred, that a catalyst may be activated in a first reactor and then furnished to a subsequent reactor in which the desirable reaction to be catalysed is carried out.

The catalyst may be packed in a reaction zone of a reactor, located on trays within the reactor or located in catalyst carriers such as those described in WO2011/048361 and WO2016/050520, the contents of which are incorporated herein by reference.

The catalyst may be any suitable catalyst which can be activated in the liquid phase by reaction with a reducing agent. The catalyst contained in the reactor may be a mixture of catalysts. In particular, the catalyst is a copper containing catalyst. For example, the catalyst may be a copper/chromium catalyst, which may include nickel or barium, a copper/nickel catalyst, copper/zinc catalyst, or a copper/zirconium catalyst. Other metals may also be present in the catalysts. Promotors may additionally or alternatively be present. Such catalysts are known to persons skilled in the art. Copper containing catalysts are particularly preferred for use in the present invention as they find utility in the hydrogenation of aldehydes to alcohols, where in situ activation is favoured and production downtime would be advantageously minimised by use of a liquid phase activation process in accordance with the present invention.

The catalyst may be in any suitable form, if it is solid, so that it forms a heterogeneous mixture with the liquid feed stream fed to the reactor. For example, the catalyst may be in the form of a powder, a tablet, a cylinder, an extrudate, a tri-lobe cylinder, a sphere, or mixtures thereof.

The catalyst may be provided on a support. Any suitable support may be used. For example, the catalyst may be supported on alumina, silica, chromia, zirconia, carbon or mixtures thereof.

The liquid feed stream fed to the reactor in step (b) may be any suitable liquid in which the activation reaction will take place. Preferably, the liquid will be a product produced in the reaction in which the catalyst will be used. Where the catalyst is to be used in the production of the alcohol from aldehyde, the liquid will suitably be an alcohol. Thus, for example, where the hydrogenation reaction in which the catalyst is to be used will produce butanol, butanol will be used as the liquid feed stream for the activation process of the present invention.

The liquid feed stream will generally contain some water. However, it is a feature of the present invention (amongst others) that the concentration of the water in the feed stream may be controlled such that the liquid stream recovered in step (d) has a peak water concentration of less than 1.5 wt %. This control may be achieved by utilising a "dry" liquid feed, such as an alcohol or an alkane, having a water concentration in the liquid feed stream of 0.1 wt % or less. The water concentration of the liquid feed stream may be 0.05 wt % or less.

In the present activation process, any suitable reducing agent may be used. Generally, the reducing agent will be a gaseous reducing agent. The reducing agent may preferably be hydrogen. The reducing agent may be added to the reactor continuously or in pulses.

Any suitable concentration of reducing agent may be used. In one arrangement, the initial concentration of reducing agent may be from about 2 mol % to about 100 mol %, from about 5 mol % to about 50 mol %. The person skilled in the art will appreciate that the concentration of reducing agent may be varied as an activation rate control mechanism.

The concentration of the reducing agent may change as the activation process proceeds. For example, the concentration may increase as the activation process proceeds. Any suitable rate of increase in concentration of the reducing agent may be used, incremental increases of about 10 mol % are preferred, until a final desired concentration is reached.

It will, therefore, be appreciated that as the activation reaction progresses, the concentration of the reducing agent may increase from a starting level of about 5 mol % to a final concentration of about 100 mol %, or the concentration of the reducing agent may increase from a starting level of about 5 mol % to a final concentration of about 50 mol % to about 100 mol % during the activation process.

Suitably, the liquid feed stream and the reducing agent may be supplied separately, or they may be combined before being fed to the reactor. Where a recycle stream is supplied in step (b) it may be supplied directly to the reactor or it may be combined with one, or both, of the liquid feed stream and the reducing agent before being supplied to the reactor.

The activation process may be carried out in the presence of an inert gas. Any suitable inert gas may be used. Suitable inert gas may be argon or nitrogen. Some advantages may be noted when nitrogen is the inert gas such as cost or availability. The inert gas will generally be provided to the reactor in combination with the reducing agent.

The activation process will be carried out under any suitable reaction conditions. The activation process is performed at any suitable temperature and any suitable pressure. The temperature and pressure provided in the reactor will depend on the liquid feed and/or reducing agent that is used and the catalyst that is to be activated. The starting temperature and the maximum temperature may be known from previous experience with the selected liquid feed, reducing agent and catalyst, the structure and packing of the reactor and whether a recycle is present. Alternatively, the starting temperature and maximum temperature may be determined experimentally such as by differential scanning calorimetry (DSC). Preferably, when activating catalysts suitable for use in a process of hydrogenation of an aldehyde to alcohol the activation temperature will not exceed 200° C.

More especially, the process may be carried out between the initial ambient temperature to about 200° C. However, other temperature ranges may be used such that the process may be carried out between a temperature of about 130° C. to about 180° C.

The temperature may be increased during the process from the initial ambient temperature to an operating temperature (in some cases activation of the catalyst will only begin once a threshold activation temperature has been reached, although this will depend upon the catalyst to be activated, and this will be known to the person skilled in the art). The temperature may be increased by heating the liquid feed stream. Additionally, or alternatively, the temperature may be increased by heating the recycle stream where present, and this is a preferred feature of the present invention. Any suitable rate of temperature increase may be used.

Each incremental increase in temperature may be maintained for a suitable period of time. The suitable period of time may be one or more of:
that required for the concentration of the reducing agent exiting the reactor to be the same as the concentration of the reducing agent being introduced into the reactor;
when no further exotherm is observed; and,
when water generation has ceased.

Each incremental increase in temperature may be maintained for a period of at least about 90 minutes, at least about 120 minutes, or at least about 150 minutes.

Suitably a positive total gas pressure should be provided during the activation process. Preferably, the total gas pressure during activation may be at least about 0.1 bar above the vapour pressure of the liquid feed stream at the operating temperature, and preferably at least about 0.3 bar, at least about 1 bar, at least about 2 bar, or at least about 4 bar. The upper limit of the pressure towards the end of the activation process should preferably approach the subsequent catalysed process reaction pressure (generally at least 20 barg), so that the reactor is in a ready state for performance of the catalysed reaction process with minimal loss of time.

The temperature of the catalyst in the reactor may preferably be monitored during the activation process. An exotherm may be observed during the activation process. Control of the observed exotherm is preferable to ensure that overheating of the catalyst is avoided. As such, if the exotherm is greater than a particular level, such as about 20° C. (depending of the catalyst to be activated), it is preferable to cool the catalyst bed. As such the activation process may include the step of cooling the liquid feed stream prior to providing it to the reactor. Additionally, or alternately, it is preferable where a recycle is present, in the event that the exotherm is greater than a particular level, such as about 20° C., that the recycle be cooled before it is returned to the reactor to reduce the temperature within the reactor.

However, where appropriate, one or more of the liquid feed stream, the reducing agent and the recycle stream, where present, may be heated before being added to the reactor. Heating may be required at any suitable time such as prior to the start of the activation process, or if the activation process appears to tail off (as indicated by an observed reduction in the exotherm, or water production rate). Different streams may be heated at different times as required. This may also be appropriate at other stages within the activation process. During the operation of the process, the recycle stream, where present, will be the preferred stream to be heated. The recycle stream may be heated at any suitable rate. For example, it may be heated at a rate of about 5° C./h (hour), about 10° C./h, or about 15° C./h.

The flow of the liquid stream over the catalyst may be from about 5 to about 150 $m^3/m^2h$.

As alluded to above, maintaining a peak water concentration of less than 1.5 wt %, may be achieved by selection of the rate at which the liquid stream is removed from. Thus, the rate of removal can be altered during the term of the reaction. The water concentration in the recovered liquid stream is controlled by the rate of activation (i.e. the reducing agent supply rate in step (b)) and liquid stream removal (in step (d)). The activation process is suitably operated with an overall fixed liquid inventory—so the removal rate of the liquid stream in step (d) is a function of the supply of the fresh flow of supplied liquid feed stream to the reactor or the supply feed rate of the liquid feed stream is a function of the recovery rate of the liquid stream from the reactor.

The peak water concentration may additionally or alternatively be controlled by the removal of water produced in the reactor. This may be achieved by means of a liquid and/or a gaseous purge. However, this means for controlling the peak water concentration will be more appropriate in some circumstances. For example, it may be appropriate where the catalyst is to be used in producing higher alcohols such as iso-nonyl alcohol, 2-propyl heptanol or detergent range alcohols. The person skilled in the art will appreciate that there is lower solubility of water in higher alcohols, so the removal of water in the vapour phase is possible for higher alcohols due to the increased difference in boiling point. Therefore, where higher alcohols are employed as the liquid feed stream the activation process can run at a pressure which enables removal of water as a vapour whilst the higher alcohol remains as a liquid.

Prior to the activation process of the present invention, the catalyst may be subjected to wetting. The wetting process will generally be carried out by backfilling the reactor such that the catalyst is submerged in a suitable wetting liquid. Preferably, the wetting liquid may be the liquid which will be supplied in step (b) of the activation process of the present invention or alternatively a different liquid may be used.

As part of the wetting process the catalyst will generally be soaked for a period of time that is sufficient to saturate at least a substantial portion of the catalyst pores, and preferably substantially all of the catalyst pores. In order to assist saturation into the pores of the catalyst, the reactor will preferably be pressurised during wetting. This will generally be achieved by maintaining the reactor under an inert gas, such as nitrogen, at pressure. Any suitable pressure may be used. Pressures of about 0.2 MPa(g) to about 0.4 MPa(g) may be used, such as about 0.3 MPa (g). An exotherm may be noted during the wetting process.

Following wetting, any water present, which may have been produced as part of the wetting process or may be residual in the reactor, may be removed by purging the reactor with fresh liquid, this fresh liquid may suitably employ further wetting liquid or employ the activation process liquid feed stream. The water content following the purge may preferably be less than about 1.5 wt %, and more preferably about 1.0 wt %.

Additionally, the release of water from the catalyst during initial warm up at the start of the activation process may be observed and thus there may be a requirement to remove this water by purging the reactor during this initial temperature ramp to maintain the water concentration as low as possible, and preferably less than about 1.5 wt %, and more preferably about 1.0 wt %.

Once activated by the process of the present invention the catalyst may be used to catalyse a reaction. Generally, the catalysed reaction is preferably performed in the same reactor, but subsequent to the activation of the catalyst. In particular, the catalyst activated in accordance with the present invention will be used in the hydrogenation of aldehydes to the corresponding alcohol. Thus, according to a further aspect of the present invention there is provided a process for hydrogenating an aldehyde comprising contacting an aldehyde with hydrogen in the presence of a catalyst activated in accordance with a process as describe above. More especially, the hydrogenation of an aldehyde to the corresponding alcohol is performed in the reactor with the activated catalyst in situ, that is preferably the catalysed reaction is performed in the same reactor vessel as the activation process. As such, it is a preferred feature of the activation process that, following activation of the catalyst, the reactor and/or catalyst bed be adjusted to a temperature suitable for carrying out the desired catalytic reaction. Furthermore, the liquid feed stream of step (b) is switched to the desired feed stream for the desired reaction.

Where the desired reaction is the preferred hydrogenation of an aldehyde to an alcohol reaction, the reaction feed stream is switched to an aldehyde, and this may be any suitable aldehyde. More especially, the aldehyde may be branched or unbranched, saturated or unsaturated. The aldehyde may have from 4 to 16 carbon atoms. Suitable aldehydes include butyraldehyde, valeraldehyde, 2-ethyl hexenal, 2-propyl heptenal, iso-nonyl aldehyde or detergent range aldehydes.

The present invention will now be described, by way of example, with reference to the accompanying figures in which.

It will be understood by those skilled in the art that the drawings are diagrammatic and that further items of equipment such as feedstock drums, pumps, vacuum pumps, compressors, gas recycling compressors, temperature sensors, pressure sensors, pressure relief valves, control valves, flow controllers, level controllers, holding tanks, storage tanks and the like may be required in a commercial plant. Provision of such ancillary equipment forms no part of the present invention and is in accordance with conventional chemical engineering practice.

Figure 1:
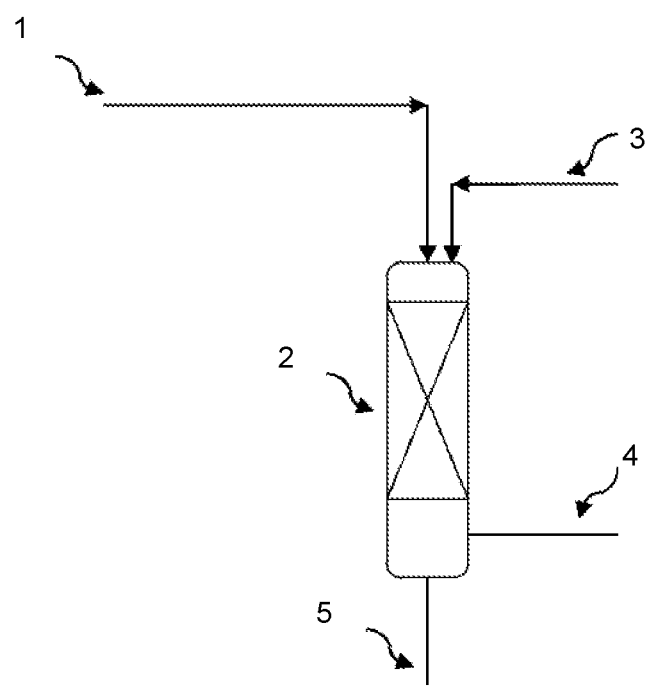
FIG. 1 is a schematic diagram of the process of the present invention.

As illustrated in FIG. 1, a liquid feed stream is fed in line 1 to reactor 2 containing a catalyst. Gaseous reducing agent is fed in line 3 to the reactor 2. As illustrated the liquid stream and the gaseous reducing agent are fed separately. However, alternatively, they may be combined before being fed to the reactor 2.

A gaseous purge will be removed in line 4 and liquid stream is removed in line 5. During the activation process the peak water concentration in the steam recovered in line 5 will be substantially maintained at less than 1.5 wt %. Where the stream is found to have a peak water content equal to or above 1.5 wt %, the water content of the stream added to the reactor in line 1, or the rate of removal of liquid stream 5 may be adjusted to achieve the required peak water content. Additionally, or alternatively, water may be removed from the reactor in a liquid and/or gas purge.

Figure 2:
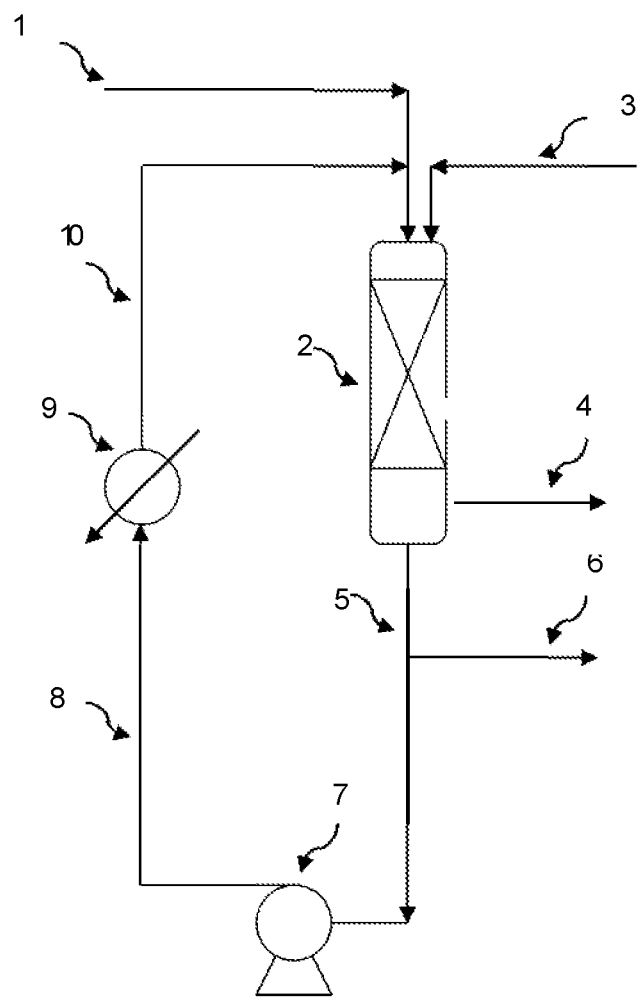
FIG. 2 is a schematic diagram of an alternative arrangement of the process of the present invention.

An alternative arrangement is illustrated in FIG. 2. As in FIG. 1, a liquid feed stream is fed in line 1 to reactor 2 containing a catalyst. Gaseous reducing agent is fed in line 3 to the reactor 2. As illustrated the liquid feed stream and the gaseous reducing agent are fed separately. However, alternatively, they may be combined before being fed to the reactor 2. A gaseous purge will be removed in line 4 and liquid stream is removed in line 5.

In this alterative arrangement, the liquid stream recovered in line 5 is separated with a recovery stream removed in line 6. The remainder of the liquid stream is pumped for treatment using pump 7 via line 8 to a heat exchanger 9 before being recycled to the reactor 2 in line 10. In the illustrated arrangement, the stream recycled in line 10 is mixed with the liquid feed stream 1 before they are added to the reactor 2. However, it will be understood that the recycle stream 10 may be fed directly to the reactor or it may be combined with the gaseous reducing agent or both the gaseous reducing agent and the liquid feed stream.

Generally, the recycle stream will be cooled in the heat exchanger 9 before being recycled to the reactor 2 in line 10. However, where appropriate the heat exchanger may be used to heat the recycle stream. For example, heating may be required during start-up of the activation process.

As described above there are various options which may be used in the process of the present invention. To aid understanding one example of the activation process of the present invention is set out below. However, it will be understood that this example is simply to assist in understanding and is not limiting.

Activation Process for an Aldehyde to Alcohol Hydrogenation Catalyst

A commercially available oxidised copper containing catalyst with a chromium promoter, known to be suitable for hydrogenation of aldehyde ethyl propyl acrolein (EPA, 2-ethyl hexenal), is loaded into a reactor (the reactor also being suitable for the performance of the hydrogenation of the aldehyde to its corresponding alcohol). The catalyst is a solid heterogenous catalyst provided as a catalyst bed in the reactor.

Prior to the catalyst being rendered in a form suitable to act as a catalyst for the aldehyde conversion reaction it is necessary that the oxidized catalyst be activated by means of reduction. In accordance with the present invention the activation may be advantageously performed utilizing a hydrogen gas as a reducing agent whilst providing an inert liquid feed stream; in this case the liquid feed stream is "dry" butanol (99+%) with a water content below 0.1 wt %. The liquid feed stream acts as a heat sink for the exothermic reduction of the copper containing catalyst to avoid the problems associated with overheating. However, accumulated water levels as low as 2.5 wt % have been found to adversely affect the final activity of the catalyst for its intended use, and in accordance with the present invention control of the activation process water levels, as observed in the recovered liquid stream, is advantageous.

Once the catalyst bed has been loaded into the desired reactor a catalyst wetting procedure is employed as an initial step, prior to commencing the catalyst activation process. "Dry" butanol is fed into the reactor as the catalyst wetting liquid. As such in this example the butanol is utilised as both the wetting liquid, and later, as the activation liquid feed stream. In alternative arrangements, the wetting liquid and activation liquid feed stream may vary. A positive pressure is maintained in the reactor to ensure that the liquid remains in its liquid state. Suitably a pressure of between 0.1 and 0.4 MPa is achieved by supplying nitrogen as an inert gas stream. A wetting liquid recycle loop is established, and sufficient butanol is fed into the reactor to allow the catalyst to be wetted and to fill the pipes, vessels and pump of the wetting liquid recycle loop; once sufficient wetting liquid is provided introduction of further wetting liquid is stopped. It is not necessary that the wetting liquid be recycled through the reactor during the wetting process, however, in the present example this was carried out to ensure that wetting liquid flows through the catalyst bed and achieves adequate wetting in a good time.

During the wetting procedure, a sample of the recirculating wetting liquid is removed and the concentration of any water present in the liquid is analysed for. In the case that the concentration of water present is unacceptably high the removal of water is necessary. Reduction of the water concentration to less than 1.5 wt % (if necessary), prior to beginning the activation process is suitable, and in the present case a reduction to 1.5 wt % was achieved by the introduction of fresh butanol feed into the reactor, whilst recycle of the butanol used for the wetting procedure continues via the recycle loop.

Once the catalyst has been fully wetted, and the level of water in the recirculating wetting liquid is reduced to less than 1.5 wt % the activation process may begin.

Throughout the wetting process inert nitrogen gas has been fed into the reactor to establish a positive pressure, and this positive pressure is maintained for the activation process which follows. Hydrogen, which will act as the reducing agent, is now introduced to the nitrogen gas stream up to a level of 30 mol % of the total nitrogen gas stream. Once the reducing agent is introduced to the reactor the temperature of the catalyst bed in the reactor should be monitored. Initially, the temperature of the catalyst bed is raised via heating of the butanol passing through the recycle loop which is reintroduced into the reactor, alongside any further butanol liquid feed stream which may be introduced to the reactor. The heating of the catalyst bed is controlled to provide a maximum temperature increase of 5° C. per hour. In this way, localized overheating of the catalyst in the catalyst bed may be avoided. Heating is continued until a temperature of about 130° C. is achieved, which is the initial temperature at which activation is established for the copper containing catalyst. Once activation is in progress the temperature of the catalyst bed is to be maintained at about 130° C. by the exothermic nature of the reduction reaction, and by heating and/or cooling the butanol recycle stream as necessary. More especially, where a temperature rise of more than 20° C. is observed then the recycled butanol stream should be cooled. Throughout this activation procedure the butanol stream removed from the reactor for recycling is sampled and monitored for water concentration. When the water concentration of the stream removed from the reactor approaches 1.5 wt % then the rate of introduction of fresh butanol in the liquid feed stream and the rate of removal of the butanol from the reactor are adjusted up until the water concentration is maintained at below 1.5 wt %. The introduction of hydrogen can also be reduced or ceased to prevent any more water being produced in the reactor which will allow the water concentration to be reduced when feeding in fresh liquid feed whilst removing some butanol from the reactor.

Once the activation process has proceeded to a point at which the level of hydrogen in the inert nitrogen gas stream exiting the reactor equals 30 mol %, and the temperature of the catalyst bed has stabilised such that no temperature rise is observed, and water generation has ceased then the hydrogen concentration may be increased in 10 mol % increments to 100 mol %.

In addition, at this stage the pressure in the reactor may be increased up to no more than 1.5 MPa, and the temperature observed in the catalyst bed is now closely monitored to ensure that it does not exceed 150° C., and is substantially maintained at 130° C. Control of the catalyst bed temperature is achieved as described above. If the temperature rise in the catalyst bed is deemed to be too high then the pressure increase should be halted until the temperature of the catalyst bed stabilizes. Throughout this procedure the water concentration of the removed butanol liquid stream is sampled and the concentration of water controlled at a level of less than 1.5 wt % as described above.

When there is no temperature increased observed, and no further water generation then the temperature of the catalyst bed is increased to 150° C. in 5° C. per hour increments. Each temperature increase increment is maintained for 2 hours to allow the temperature across the catalyst bed to stabilise and avoid localized overheating. During this heating ramp the butanol recycle and feed streams are maintained and sampled to ensure no further reduction is occurring.

Once the reactor pressure has been increased, and the temperature rise has stabilized at 150° C., the water concentration in the butanol removed for recycle has stopped increasing, and no hydrogen is being consumed, then the catalyst activation is deemed to be complete.

Once the activation of the catalyst is deemed to be complete then the reactor with the activated catalyst in situ may be readied for use in the subsequent process of hydrogenation of an aldehyde feed. More especially, the temperature of the catalyst bed may be reduced via the cooling of the recycle of the butanol stream which continues to be reintroduced to the reactor. Additionally, the hydrogen gas stream may be replaced or diluted with an alternative gas stream. Suitable hydrogenation reaction conditions are known to the person skilled to the art.

Although the above example concerns a copper containing catalyst for use in hydrogenation of an aldehyde, similar activation processes can be employed to activate other oxidised catalysts.

EXAMPLES

The present invention will now be described by way of example with reference to the following Examples and Comparative Examples.

In examples 1 to 4 the reactor was charged with 250 ml catalyst (⅛" tablets 50% CuO 50% $Cr_2O_3$) in all examples.

Comparative Example 1

A gas phase activation was performed using a stream of 1.7 mol % hydrogen in nitrogen which was passed over the catalyst at 100 NL/h and the bed temperature raised to approximately 175° C. The exotherm was followed as it moved down the catalyst bed and the temperatures stabilised after 30 hours. The hydrogen concentration was then incrementally increased to 100 mol %, before increasing the pressure from approximately 0.1 MPa to 2 MPa. The bed temperatures were reduced to 100° C. before wetting the catalyst with butanol and establishing recycle flow prior to introduction of aldehyde feed and the assessment of the catalysts activity.

In each of the following examples, the liquid phase activation procedure used is as described above with any modifications described in the example details provided below.

Comparative Example 2

In this example, the activation liquid feed was crude butanol containing 0.4 wt % water. No butanol recovery was applied and no water was removed from the reactor during the liquid phase activation process. The peak water level concentration reached was 2.55 wt. %. As such, this comparative example represents a typical known liquid phase activation method where water concentration is not controlled.

Example 3

In this example, the activation liquid feed was pure n-butanol (containing less than 0.1 wt % water) and a continuous butanol recovery rate is employed to control the concentration of water in the liquid stream. The peak water level reached was 1.27 wt %.

Comparative Example 4

Comparative Example 4 was performed to confirm the effect of increasing the water concentration. In this example, the activation liquid feed was crude butanol. Additional water was dosed in the circulating butanol prior to activation to give an initial water concentration of 3.4 wt %. No recovery of the butanol was performed to limit the water concentration. The peak water concentration was 6.29 wt %. It will be understood by the person skilled in the art that the relative volume of catalyst/liquid inventory is significantly reduced on an experimental rig, such as that used for the present examples as compared to a commercial unit, and so the dosing of additional water in this example was required to give an experimental peak water concentration close to the peak water levels seen on commercial units.

After completion of each of the activation procedures described above, the activity of the reduced catalyst was measured in a hydrogenation process test using a mixed butyraldehyde feedstock which contained >95 wt % aldehydes (n:i ratio in the range 6-12:1). The conditions for the activity tests are given in Table 1 below:

TABLE 1

| Aldehyde Feed Rate | LHSV* = 1 |
| --- | --- |
| Inlet Temperature, ° C. | 150 |
| Peak Temperature, ° C. | 168 |
| Recycle to Feed Ratio | 20:1 |
| Vent Flow Rate, nL/h | 10 |

*= Liquid hourly space velocity

A summary of experiments performed under these standard conditions showing the effect of observed peak water concentration during the activation process on the subsequent catalyst activity for mixed butyraldehyde hydrogenation using commercial copper-chrome catalyst are set out in Table 2. The catalyst activity is measured as the aldehyde slip during the initial period of operation at the standard conditions above.

TABLE 2

| | Activation Comments | Peak Water During Activation (wt %) | Aldehyde Slip (ppm) |
| --- | --- | --- | --- |
| Comparative Example 1 | Gas Phase | N/A | 301 |
| Comparative Example 2 | Crude Butanol used (0.4 wt % water) | 2.55 | 985 |
| Example 3 | Dry Butanol—Continuous Removal | 1.27 | 361 |
| Comparative Example 4 | High Initial Water | 6.29 | 1381 |

It can therefore be seen that the catalyst activated in accordance with the processes of the present invention produced an activation which was similar in performance to that activated in gas phase activation.

Temperature programmed reaction studies support the observations of the impact of water being present in the activation process on reducing surface area which it is believed leads to the reduced activity in the subsequent aldehyde hydrogenation process. In this experiment, the effect of the presence of water in the reducing atmosphere (referred to as a "wet" atmosphere) on the copper metal area of two catalysts was investigated.

1. A sample of a copper-chromite catalyst was reduced in a water/hydrogen/helium stream comprising 2.5 mol % water and 5 mol % hydrogen at a temperature of from ambient to 220° C. Similarly, a sample was reduced in a hydrogen/helium stream comprising 5 mol % hydrogen at a temperature of from ambient to 220° C. The copper metal areas of the sample were measured by $N_2O$ decomposition at 60° C. The obtained relative copper surface areas from reactive frontal chromatograms of $N_2O$ decomposition on samples following reduction in dry atmosphere or in wet atmosphere are shown in Table 3, below. Reduction in a "wet" atmosphere leads to a reduction in the measured copper surface area.

Table 3 shows the measured relative copper surface area from Reactive Frontal Chromatograms of $N_2O$ decomposition over the copper-chromite catalyst following temperature programmed reduction (TPR) of the sample in either an $H_2$/He stream or a $H_2/H_2O$/He stream

TABLE 3

| Activation Stream | Relative Active Copper Surface Area |
|---|---|
| 2.5 mol % $H_2O$/5 mol % $H_2$/He | 0.7 |
| 5 mol % H2/He | 1.0 |

2. A sample of a copper-alumina catalyst was reduced in a water/hydrogen/helium stream comprising 2.8 mol % water and 5 mol % hydrogen at a temperature of from ambient to 220° C. Similarly, a sample was reduced in a hydrogen/helium stream comprising 5 mol % hydrogen at a temperature of from ambient to 220° C. The copper metal areas of the sample were measured by $N_2O$ decomposition at 60° C. The obtained relative copper surface areas from reactive frontal chromatograms of $N_2O$ decomposition on samples following reduction in dry atmosphere or in wet atmosphere are shown in Table 4 below. Reduction in a "wet" atmosphere leads to a reduction in the measured copper surface area.

Table 4 shows the measured relative copper surface areas from Reactive Frontal Chromatograms of $N_2O$ decomposition over a copper-alumina catalyst following temperature-programmed reduction (TPR) of the sample in either an $H_2$/He stream or a $H_2/H_2O$/He stream

TABLE 4

| Activation Stream | Relative Active Copper Surface Area |
|---|---|
| 2.8 mol % $H_2O$/ 5 mol % $H_2$/He | 0.8 |
| 5 mol % H2/He | 1.0 |

The invention claimed is:

1. A process for activation of a catalyst comprising:
   (a) providing a reactor comprising a solid catalyst which is to be activated by reduction;
   (b) supplying a liquid feed stream and a reducing agent to the reactor;
   (c) operating the reactor such that the reducing agent causes activation of the catalyst;
   (d) recovering a liquid stream and a gas stream from the reactor; and wherein, a peak water concentration in the liquid stream recovered in step (d) is substantially maintained at less than 1.5 wt % by one or more of:
   controlling a water concentration of the liquid feed stream supplied in step (b);
   controlling a rate of recovery of the liquid stream recovered in step (d); and,
   removal of water produced within the reactor.

2. The process according to claim 1, wherein at least a portion of the liquid stream recovered in step (d) may be recycled and supplied to the reactor in step (b).

3. The process according to claim 1, wherein the liquid stream recovered from the reactor in step (d) can be subject to a treatment and then reused (recycled) alongside the liquid feed stream to be fed to the reactor in step (b).

4. The process according to claim 3, wherein said treatment comprises a drying process.

5. The process according to claim 1, wherein the reactor provided in step (a) is that in which a subsequent reaction to be catalyzed is to be carried out, such that the activation of the catalyst is performed in situ.

6. The process according to claim 1, wherein the catalyst to be activated is a copper containing catalyst.

7. The process according to claim 1, wherein the liquid feed stream fed to the reactor in step (b) is a product produced in a subsequent reaction in which the catalyst will be used.

8. The process according to claim 7, wherein the liquid feed stream is an alcohol or alkane.

9. The process according to claim 8, wherein the liquid feed is an alcohol.

10. The process according to claim 9, wherein the liquid feed is butanol.

11. The process according to claim 1, wherein the liquid feed stream has a water concentration of 0.1 wt % or less.

12. The process according to claim 1, wherein the reducing agent is a gaseous reducing agent.

13. The process according to claim 12, wherein the reducing agent is hydrogen and wherein the reducing agent may be added to the reactor continuously or in pulses.

14. The process according to claim 1, wherein an initial concentration of reducing agent may be from about 2 mol % to about 100 mol %.

15. The process according to claim 1, wherein a concentration of reducing agent increases to a final concentration of about 100 mol % during the activation of the catalyst.

16. The process according to claim 1, wherein the liquid feed stream and the reducing agent may be supplied separately or they may be combined before being fed to the reactor.

17. The process according to claim 2, wherein the portion of the liquid stream recovered in step (d) that is recycled is supplied directly to the reactor or combined with one, or both, of the liquid feed stream and the reducing agent before being supplied to the reactor.

18. The process according to claim 1 carried out in the presence of an inert gas.

19. The process according to claim 1, wherein the process is carried out at a temperature between an initial ambient temperature to about 200° C.

20. The process according to claim 19, wherein the process is carried out at a temperature between about 130° C. to about 180° C.

21. The process according to claim 1, wherein the process temperature may be increased by heating the liquid feed stream.

22. The process according to claim 1, wherein the process temperature may be increased by heating a recycle stream where present.

23. The process according to claim 1, wherein a positive total gas pressure is provided during the activation of the catalyst.

24. The process according to claim 1, wherein the liquid stream over the catalyst has a flow that is from about 5 to about 150 $m^3/m^2h$.

25. The process according to claim 1, further comprising an initial catalyst wetting process.

26. The process according to claim 25, wherein the initial catalyst wetting process employs a wetting liquid which is the same as the liquid feel stream which will be supplied in step (b) of the activation of the catalyst.

27. The process according to claim 25, wherein following the initial catalyst wetting process, any water present is removed by purging the reactor such that the water content is less than about 1.5 wt %.

28. The process according to claim 1, wherein there is an initial warm up at the start of the activation of the catalyst, and any water present is removed by purging the reactor to maintain a concentration of water that is less than about 1.5 wt %.

29. The process according to claim 1, further comprising (e) contacting an aldehyde with hydrogen in the presence of the catalyst that is activated in step (c).

30. A process according to claim 29, wherein following activation of the catalyst, the reactor and/or catalyst bed temperature is adjusted to a temperature suitable for carrying out the hydrogenation of the aldehyde to the corresponding alcohol, including switching the liquid feed stream of step (b) of the activation process to the desired aldehyde feed stream for the hydrogenation reaction.

31. A process according to claim 29, wherein the aldehyde is selected from butyraldehyde, valeraldehyde, 2-ethyl hexenal, 2-propyl heptenal, iso-nonyl aldehyde and detergent range aldehydes.

* * * * *